United States Patent
Li et al.

(10) Patent No.: US 12,290,502 B2
(45) Date of Patent: May 6, 2025

(54) USE OF USNIC ACID, A SALT OF USNIC ACID, OR A FORMULATION THEREOF IN THE PREPARATION OF ANTI-AVIAN COCCIDIOSIS DRUGS OR FEED ADDITIVES

(71) Applicants: BEIJING CENTRE BIOLOGY CO., LTD, Beijing (CN); CENTRE (INNER MONGOLIA) BIOLOGY CO., LTD, Taipusi Banner (CN); AETHER CENTRE (BEIJING) BIOLOGY CO., LTD, Beijing (CN); XIQIN (INNER MONGOLIA) PHARMACEUTICAL CO., LTD, Taipusi Banner (CN)

(72) Inventors: Fuyuan Li, Beijing (CN); Xiumin Wang, Beijing (CN); Tianyi Wen, Beijing (CN); Aohan Li, Beijing (CN); Housheng Jiang, Beijing (CN)

(73) Assignees: BEIJING CENTRE BIOLOGY CO., LTD, Beijing (CN); CENTRE (INNER MONGOLIA) BIOLOGY CO., LTD, Taipusi Banner (CN); AETHER CENTRE (BEIJING) BIOLOGY CO., LTD, Beijing (CN); XIQIN (INNER MONGOLIA) PHARMACEUTICAL CO., LTD, Taipusi Banner (CN)

( * ) Notice: Subject to any disclaimer, the term of this patent is extended or adjusted under 35 U.S.C. 154(b) by 114 days.

(21) Appl. No.: 18/150,278

(22) Filed: Jan. 5, 2023

(65) Prior Publication Data

US 2023/0226012 A1 Jul. 20, 2023

(30) Foreign Application Priority Data

Jan. 20, 2022 (CN) .......................... 202210068161.9

(51) Int. Cl.
*A61K 31/343* (2006.01)
*A23K 20/121* (2016.01)
*A23K 50/70* (2016.01)

(52) U.S. Cl.
CPC .......... *A61K 31/343* (2013.01); *A23K 20/121* (2016.05); *A23K 50/70* (2016.05)

(58) Field of Classification Search
CPC .... A61K 31/343; A23K 50/70; A23K 20/121; A23K 20/111; A23K 20/132; A23K 50/75; A23K 50/30; A23K 31/185; A23K 33/02; Y02A 50/30
See application file for complete search history.

(56) References Cited

U.S. PATENT DOCUMENTS 5,834,473 A * 11/1998 Virtanen ............... A23K 20/105
514/556

OTHER PUBLICATIONS

Hillmas, Corey, and Daniel Fabricant. "35/Biomarkers of Toxicity for Dietary Ingredients Contained in Dietary Supplements." Biomarkers in Toxicology, 1st ed., Elsevier, 2014, pp. 609-627. (Year: 2014).*
Bastin et al. ("Salt selection and optimisation procedures for Pharmaceutical New Chemical Entities." Organic Process Research & amp; Development, vol. 4, No. 5, Jul. 19, 2000, pp. 427-435, https://doi.org/10.1021/op000018u. (Year: 2000).*
European Extended Search Report issued in European Application No. 23150524.9; mailed Apr. 25, 2023; 8 pgs.
Guven, Esin et al.; Anticoccidal Efficacy of Usnic Acid in Broilers; Kafkas Universitesi Veteriner Fakultesi Dergis; vol. 22, No. 4; Mar. 16, 2016; pp. 551-556.

* cited by examiner

*Primary Examiner* — Kortney L. Klinkel
*Assistant Examiner* — Donna M Nestor
(74) *Attorney, Agent, or Firm* — HAUPTMAN HAM, LLP

(57) ABSTRACT

Provided is a use of usnic acid or a salt of usnic acid or a formulation thereof in the preparation of anti-avian coccidiosis drugs or feed additives. Also provided are anti-avian coccidiosis drugs and feed additives comprising usnic acid or a salt of usnic acid or a formulation thereof. Both the use of usnic acid or a salt of usnic acid or a formulation thereof in the preparation of anti-avian coccidiosis drugs or feed additives and anti-avian coccidiosis drugs and feed additives comprising usnic acid or a salt of usnic acid or a formulation thereof provide a new way for treating and preventing avian coccidiosis. The addition of usnea or usnic acid or a salt of usnic acid or a formulation thereof to feedstuff may realize effective anti-avian coccidiosis.

5 Claims, 2 Drawing Sheets

USE OF USNIC ACID, A SALT OF USNIC ACID, OR A FORMULATION THEREOF IN THE PREPARATION OF ANTI-AVIAN COCCIDIOSIS DRUGS OR FEED ADDITIVES

CROSS-REFERENCE TO RELATED APPLICATIONS

The present invention claims priority to Chinese patent application No. 202210068161.9 filed on Jan. 20, 2022, and entitled "Use of usnic acid, a salt of usnic acid, or a formulation thereof in the preparation of anti-avian coccidiosis drugs or feed additives", which is incorporated by reference herein in its entirety:

TECHNICAL FIELD

The invention generally relates to the field of medicine, in particular to use of usnic acid, a salt of usnic acid, or a formulation thereof in the preparation of anti-avian coccidiosis drugs or feed additives.

BACKGROUND ART

Usnea, also known as ny Luo, Yunwucao, Laojunxu, etc., belonging to the usnea family, is the lichen of a usnea genus plant like usnea longissima and usnea diffracta vain, which is bitter, sweet and flat in nature, and is useful in resolving phlegm, clearing liver, detoxification and hemostasis, and primarily used for treating cough, phlegm, tuberculosis, phlegm malaria, headache, red eyes, corneal opacity, bloated eyes, sore toxin, breast carbuncle, traumatic bleeding, metrorrhagia, leucorrhea, rheumatic arthralgia, and hot injury. The use of usnea as a medicinal material is long in history, and is recorded in traditional medicine ancient books in Mongolian, Tibetan, Uyghur and other minority ethnic groups, wherein, in the usnea medicinal material of all ethnic groups and regions, fruticose lichen from the usnea genus is used as medicinal resources, of which usnea longissima is the most common used. The research is more focus on usnic acid in usnea, the use of usnic acid sodium is similar to that of unic acid, which is mainly focus on drug efficacy like antibiosis, anti-infection, detoxification, anti-tumor, and cosmetics.

According to Levine classification (1982), coccidia are protozoans belonging to Apicomplexa, Sporozoa, Coccidia, Eucoccidiorida, Eimeriorina and Adeleorina. Common avian coccidia in clinic mainly are *Eimeria tenella, Eimeria acervulina, Eimeria maxima, Eimeria necatrix, Eimeria brunetti, Eimeria mitis*, and *Eimeria praecox*. Avian coccidiosis is a common disease in chicken farms, and intensive chicken farms are most prone to the coccidiosis outbreak, with high morbidity and mortality. Different avian coccidia have similar life cycle, including three reproductive stages: spore reproduction, fission reproduction, and gamete reproduction.

There are many ways to evaluate the anticoccidial effect of drugs, one of which is the anticoccidial index (ACI), in which many parameters, such as survival rate, weight gain, lesion, oocyst production, and feces score, are comprehensively assessed to be used as an indicator to determine the drug resistance or drug efficacy against coccidiosis. The commonly used formula for calculating the anticoccidial index is: ACI=(relative weight gain rate+survival rate)×100−(lesion value+oocyst value).

Before the 1940s, people used various refining methods to control coccidiosis with skim milk, vinegar and sulfur powder. It was not until the early 1940s that sulfa drugs were found to have potential anticoccidial activity, and then sulfa drugs were used to treat coccidiosis. The commonly used anticoccidial drugs are mainly divided into the following classes: polyether ionophore antibiotics, chemically synthetic anticoccidial drugs, amide anticoccidial drugs, pyridine anticoccidial drugs, quinoline anticoccidial drugs, alkaloid anticoccidial drugs, etc. There are many kinds of anticoccidial drugs with different modes of action, which can play their own roles well only by reasonable action to control coccidiosis effectively. In recent years, due to the increasing drug-resistance of coccidia, the development speed of new drugs can't keep up with the emergence speed of drug-resistant strains, especially the emergence of multiple drug-resistant strains, which makes it more difficult to control avian coccidiosis. Therefore, the development of new anticoccidial drugs is an urgent need in breeding industry.

Common antiparasitic drugs reported in documents include: antifebrile dichroa root, *Artemisia apiacea, Phytolacca acinosa, quispualis indica*, cortex *Meliae, Areca catechu*, and so on. It has been reported that, in addition to usnea, there are other anti-*Toxoplasma gondii* medicinal herbs, including turmeric, antifebrile dichroa root, *Artemisia apiacea, Radix scutellariae*, liquorice root, *Radix stemonae, Cyrtomium fortunei, Areca catechu, Brucea javanica*, and so on. Most antiparasitic drugs are responsible for their respective antiparasitic ranges. It has been reported in documents that usnic acid has anti-*Toxoplasma gondii* activity, but usnea, usnic acid and usnic acid sodium have not been reported to be used for controlling avian coccidiosis.

In view of this, the invention is provided.

SUMMARY OF THE INVENTION

The invention aims to provide a novel use of usnic acid, a salt of usnic acid, or a formulation thereof, so as to provide a new way for treating avian coccidiosis.

Provided herein is use of usnic acid, a salt of usnic acid, or a formulation thereof in the preparation of anti-avian coccidiosis drugs or feed additives.

Preferably or alternatively, the usnic acid is derived from usnea.

On the other hand, the invention also provides an anti-coccidiosis drug, which comprises usnic acid, and/or a salt of usnic acid, or a formulation thereof.

Preferably or alternatively, the usnic acid in the anti-avian coccidiosis drug is derived from usnea. On the other hand, provided is an anti-coccidiosis feed additive, which comprises usnic acid, and/or a salt of usnic acid, or a formulation thereof.

Preferably or alternatively, the usnic acid in the feed additive is derived from usnea.

Preferably or alternatively, the feed additive is added in feedstuff in an amount that usnic acid and/or a salt of usnic acid is not less than 0.015‰ by mass.

Preferably or alternatively, the feed additive is added in feedstuff in an amount that usnic acid and/or a salt of usnic acid is not less than 0.05‰ by mass.

Both the use of usnic acid or a salt of usnic acid or a formulation thereof in the preparation of anti-avian coccidiosis drugs or feed additives and anti-avian coccidiosis drugs and feed additives comprising usnic acid or a salt of usnic acid or a formulation thereof provide a new way for treating and preventing avian coccidiosis. The addition of usnea or usnic acid or a salt of usnic acid or a formulation thereof to feedstuff may realize effective anti-avian coccidiosis. At the same time, the use of usnea or usnic acid or a salt of usnic acid or a formulation thereof as a means for controlling avian coccidiosis, is cost-effective, simple in use, and thus suitable for large-scale promotion.

DETAILED DESCRIPTION OF THE INVENTION

Figure 1:
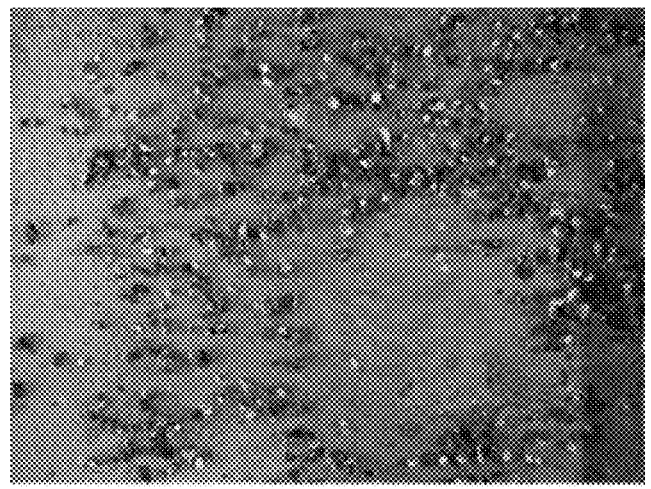
FIG. 1 is feces produced by the usnea group after *Eimeria* challenge in Example 1.

Specific embodiments of the present invention are described in detail below. It will be understood that the specific examples described herein are only used to illustrate and explain the invention, and are not intended to limit the invention.

Example 1

Usnea, turmeric, antifebrile dichroa root, *Artemisia apiacea*, liquorice root, *Radix scutellariae, Radix stemonae, Cyrtomium fortunei, Areca catechu*, and *Brucea javanica* processed according to the method of Chinese Pharmacopoeia were pulverized, and then sieved through a 200-mesh sieve for later use.

Male chicks from layer aged 1 day were selected and raised to 12-day-old. Each was weighed, while excluding thin or overweight individuals, healthy chickens with individual weight differences of less than 10 g were selected, and randomly divided into thirteen groups with each group including thirty chickens. Among them, ten groups were used as drug groups, one group as a model group, one group as a diclazuril group, and one group as a blank control group. Each chicken aged 12 days of the drug groups was subject to drug administration through mixing with feed, while that of the diclazuril group was administrated though drinking water. Each chicken aged 14 days in the drug groups, the diclazuril group and the model group was orally inoculated with $1.0 \times 10^4$ sporulated oocysts of *Eimeria tenella*. Each experimental chicken in all groups was free to feed and drink water until the test was over on the seventh day.

The experimental design is shown in Table 1.

TABLE 1

The experimental design grouping of Example 1

| Group and drug information | Number of chickens | Dosage | Administration route | Time of administration | Dose for *Eimeria* challenge ($\times 10^4$/pcs) |
|---|---|---|---|---|---|
| *Usnea* | 30 | 5 kg/ton | Mixing with feed | 2 days before *Eimeria* challenge, a total of 9 days | 1.0 |
| Turmeric | 30 | 5 kg/ton | Mixing with feed | 2 days before *Eimeria* challenge, a total of 9 days | 1.0 |
| Antifebrile dichroa root | 30 | 5 kg/ton | Mixing with feed | 2 days before *Eimeria* challenge, a total of 9 days | 1.0 |
| *Artemisia apiacea* | 30 | 5 kg/ton | Mixing with feed | 2 days before *Eimeria* challenge, a total of 9 days | 1.0 |
| Liquorice root | 30 | 5 kg/ton | Mixing with feed | 2 days before *Eimeria* challenge, a total of 9 days | 1.0 |
| Radix Scutellariae | 30 | 5 kg/ton | Mixing with feed | 2 days before *Eimeria* challenge, a total of 9 days | 1.0 |
| Radix stemonae | 30 | 5 kg/ton | Mixing with feed | 2 days before *Eimeria* challenge, a total of 9 days | 1.0 |
| *Cyrtomium fortunei* | 30 | 5 kg/ton | Mixing with feed | 2 days before *Eimeria* challenge, a total of 9 days | 1.0 |
| Areca catechu | 30 | 5 kg/ton | Mixing with feed | 2 days before *Eimeria* challenge, a total of 9 days | 1.0 |
| *Brucea javanica* | 30 | 5 kg/ton | Mixing with feed | 2 days before *Eimeria* challenge, a total of 9 days | 1.0 |

TABLE 1-continued

The experimental design grouping of Example 1

| Group and drug information | Number of chickens | Dosage | Administration route | Time of administration | Dose for *Eimeria* challenge (×10⁴/pcs) |
|---|---|---|---|---|---|
| Model group | 30 | — | — | — | 1.0 |
| Diclazuril | 30 | 0.2 ml/L | Drinking water | 2 days before *Eimeria* challenge, a total of 9 days | 1.0 |
| Blank control | 30 | — | — | — | |

The anticoccidial index (ACI) criteria were calculated by the calculation formula of Merck Corporation (USA), that is:

ACI=(relative weight gain rate+survival rate)×100− (lesion value+oocyst value).

Among them, the relative weight gain rate was calculated by
weighing each chicken at the beginning and end of the test, respectively, to calculate the average and relative weight gain rates. Relative weight gain rate=(test group weight gain rate/blank control group weight gain rate)× 100%.
The survival rate was calculated by
recording the number of dead chickens in each group, performing an autopsy to determine the cause of death, and calculating the survival rate. Survival rate=(number of chickens alive at the end of the test/number of chickens in the test group)×100%
The lesion value was calculated by
slaughtering each chicken on the 7th day after infection to take the cecum and scoring the intestinal lesion of each chicken according to the lesion scoring method designed by John Gon and Reid (1970), and converting the lesion score into the lesion value.
Lesion scoring: (in case of lesion inconsistence between both sides of cecum, the more severe shall prevail):
0 point: no macroscopic lesions;
1 point: there are a few of petechiae scattered in the cecal wall, the cecal wall is not thickened, and the contents therein are normal;
2 points: the lesion number is more, the cecum contents are obviously bloody, the cecal wall is slightly thickened, and the contents therein are normal;
3 points: there is a lot of blood or there is a cecum core (blood clot or off-white cheese-like banana-shaped blocks) in the cecum, the cecal wall is obviously thickened, and the feces contents in the cecum are poor;
4 points: the cecum swells due to being full of a large amount of blood or cecum core with or without fecal residue, and it is also scored 4 points when the chicken dies for coccidiosis.

Lesion value (0-40)=average lesion score (0-4) for each test group×10

The oocyst value and the relative oocyst production (ROP) were calculated by
collecting the chicken feces of each group, counting the number of oocysts in the feces according to McMaster counting, calculating the number of oocysts per gram of feces of each group, and obtaining the oocyst value by conversion according to Table 2.

TABLE 2

Conversion between oocyst number and oocyst value

| Number of oocysts in the test group/number of oocysts in the model group (%) | <1 | 1 ≤ 25< | 25 ≤ 50< | 50 ≤ 75< | 75≤ |
|---|---|---|---|---|---|
| Oocyst value | 0 | 5 | 10 | 20 | 40 |

Relative oocyst production (ROP)=(average oocyst production in the test group/average oocyst production in the model group)×100%. ROP≥15%, resistant to drugs: ROP<15%, no drug resistance.
The criteria for determining the drug efficacy were: ACI>180, high efficacy against coccidiosis; 160<ACI<180, medium efficacy against coccidiosis: 120<ACI<160, low efficacy against coccidiosis: ACI<120, inefficacy against coccidiosis.
The results are shown in Table 3.

TABLE 3

The test results of Example 1

| Group | Relative weight gain rate/% | Survival rate/% | Lesion value | Oocyst value | ACI value | Relative oocyst production (ROP) | Criteria |
|---|---|---|---|---|---|---|---|
| Usnea | 93.9 | 100 | 3.5 | 5 | 185.4 | 11.2 | High efficacy |
| Turmeric | 96.2 | 100 | 13.2 | 40 | 143.0 | 63.2 | Low efficacy |
| Antifebrile dichroa root | 95.0 | 100 | 10.6 | 20 | 164.4 | 43.8 | Medium efficacy |
| *Artemisia apiacea* | 89.3 | 100 | 14.0 | 20 | 155.3 | 54.9 | Low efficacy |

TABLE 3-continued

The test results of Example 1

| Group | Relative weight gain rate/% | Survival rate/% | Lesion value | Oocyst value | ACI value | Relative oocyst production (ROP) | Criteria |
|---|---|---|---|---|---|---|---|
| Liquorice root | 82.1 | 93.3 | 18.2 | 40 | 117.2 | 103.2 | Inefficacy |
| Radix Scutellariae | 88.3 | 100 | 15.4 | 40 | 132.9 | 78.9 | Low efficacy |
| Radix stemonae | 72.6 | 100 | 17.8 | 40 | 114.8 | 96.8 | Inefficacy |
| Cyrtomium fortunei | 74.3 | 100 | 16.9 | 40 | 117.4 | 98.7 | Inefficacy |
| Areca catechu | 79.2 | 100 | 15.2 | 40 | 124.0 | 78.2 | Low efficacy |
| Brucea javanica | 88.7 | 100 | 14.6 | 40 | 134.2 | 86.3 | Low efficacy |
| Model group | 73.8 | 93.3 | 17.6 | 40 | 109.5 | 100.0 | — |
| Diclazuril | 101.2 | 100 | 0.0 | 0 | 201.2 | 0.0 | High efficacy |
| Blank control | 100.0 | 100 | 0.0 | 0 | 200.0 | 0.0 | — |

Clinical Symptoms

Figure 4:
FIG. 4 is a state diagram of chickens of the model group in Example 1 after *Eimeria* challenge.

The tested chickens in the model group after infection with sporulated oocysts gradually experienced reduced food intake and poor mental health (FIG. 4). On the 4th day after infection, the drug groups (except the usnea group) and the model group suffered different levels of bloody stool and reduced food intake, and became more severe on the 5th and 6th days; the usnea group, the diclazuril group and the blank control group all had no bloody stool, without obvious abnormality in food intake and water consumption.

Bloody Stool

Figure 2:
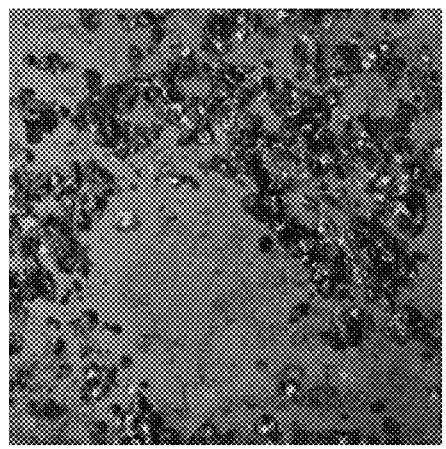
FIG. 2 is feces produced by the antifebrile dichroa root group after *Eimeria* challenge in Example 1.
Figure 3:
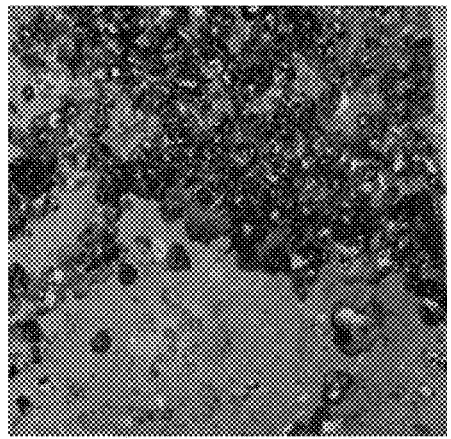
FIG. 3 is feces produced by the liquorice root group after *Eimeria* challenge in Example 1.

As shown in FIGS. 1-3, the bloody stool of each group was observed on the 5th day after *Eimeria* challenge, and feces from the groups of antifebrile dichroa root (FIG. 2) and *Artemisia apiacea* was partially mixed with blood; a large amount of feces from the groups of turmeric, liquorice root (FIG. 3), *Radix scutellariae, Radix stemonae, Cyrtomium fortunei, Areca catechu, Brucea javanica* and the model was mixed with blood; feces from the groups of usnea (FIG. 1), diclazuril and blank control was bloodless.

From the above results, the model group control and blank control tested in this example were true; the diclazuril group as a positive control group had a high therapeutic effect against *Eimeria tenella*; while usnea showed a better effect against avian coccidiosis compared with other nine herbs that have been reported to be resistant to toxoplasmosis.

Example 2

Drug group 1:3 parts of usnic acid and 97 parts of glucose, mixing well
Drug group 2:3 parts of usnic acid sodium and 97 parts of glucose, mixing well
Drug group 3:3 parts of usnic acid sodium and 2 parts of sodium hydroxide, dissolved in 95 parts of water, mixing well Male chicks from layer aged 1 day were selected and raised to 12-day-old. Each was weighed, while excluding thin or overweight individuals, healthy chickens with individual weight differences of less than 10 g were selected, and randomly divided into 6 groups with each group including thirty chickens. Among them, three groups were used as drug groups, one group as a model group, one group as a diclazuril group, and one group as a blank control group. Each chicken of the drug groups and the diclazuril group aged 12 days was subject to drug administration, with Drug groups 1 and 2 being administrated through mixing with feed, while Drug group 3 and the diclazuril group being administrated through water drinking. Each chicken aged 14 days in the drug groups, the diclazuril group and the model group was orally inoculated with $1.0 \times 10^4$ sporulated oocysts of *Eimeria tenella*. Each experimental chicken in all groups was free to feed and drink water until the test was over on the seventh day.

The experimental design is shown in Table 4.

TABLE 4

The experimental design grouping of Example 2

| Group and drug information | Number of chickens | Dosing concentration | Administration route | Time of administration | Dose for *Eimeria* challenge ($\times 10^4$/pcs) |
|---|---|---|---|---|---|
| Drug group 1 | 30 | 5 kg/ton | Mixing with feed | 2 days before *Eimeria* challenge, a total of 9 days | 1.0 |

TABLE 4-continued

The experimental design grouping of Example 2

| Group and drug information | Number of chickens | Dosing concentration | Administration route | Time of administration | Dose for *Eimeria* challenge (×10⁴/pcs) |
|---|---|---|---|---|---|
| Drug group 2 | 30 | 5 kg/ton | Mixing with feed | 2 days before *Eimeria* challenge, a total of 9 days | 1.0 |
| Drug group 3 | 30 | 1:400 | Drinking water | 2 days before *Eimeria* challenge, a total of 9 days | 1.0 |
| Model group | 30 | — | — | — | 1.0 |
| Diclazuril | 30 | 0.2 ml/L | Drinking water | 2 days before *Eimeria* challenge, a total of 9 days | 1.0 |
| Blank control | 30 | — | — | — | — |

In this example, the ACI was calculated in the same way as in Example 1.

The test results of this example are shown in Table 5.

TABLE 5

The test results of Example 2

| Group | Relative weight gain rate/% | Survival rate/% | Lesion value | Oocyst value | ACI value | Relative oocyst production (ROP) | Criteria |
|---|---|---|---|---|---|---|---|
| Drug group 1 | 97.8 | 100 | 4.1 | 5 | 188.7 | 13.2 | High efficacy |
| Drug group 2 | 96.4 | 100 | 3.6 | 10 | 182.8 | 14.3 | High efficacy |
| Drug group 3 | 97.2 | 100 | 2.9 | 5 | 189.3 | 11.8 | High efficacy |
| Model group | 80.2 | 96.7 | 17.5 | 40 | 119.4 | 100 | Inefficacy |
| Diclazuril | 98.9 | 100 | 0 | 0 | 198.9 | 0 | High efficacy |
| Blank control | 100 | 100 | 0 | 0 | 200.0 | 0 | |

Clinical Symptoms

The tested chickens in the model group after infection with sporulated oocysts gradually experienced reduced food intake and poor mental health, and became more serve on the 4-6th days after infection. Drug groups 1-3, the diclazuril group and the blank control group had no bloody stool, without obvious abnormality in food intake and water drinking.

From the above results, the model group control and blank control tested in this example were true; the diclazuril group as a positive control group had a high therapeutic effect against *Eimeria tenella*; Drug groups 1-3 also showed a high effect against avian coccidiosis, that is, both usnic acid and usnic acid sodium showed a high effect against avian coccidiosis.

Example 3

Drug group 1:0.3 parts of usnic acid sodium and 99.7 parts of glucose, mixing well
Drug group 2:0.5 parts of usnic acid sodium and 99.5 parts of glucose, mixing well
Drug group 3:1 part of usnic acid sodium and 99 parts of glucose, mixing well Male chicks from layer aged 1 day were selected and raised to 12-day-old. Each was weighed, while excluding thin or overweight individuals, healthy chickens with individual weight differences of less than 10 g were selected, and randomly divided into 6 groups with each group including thirty chickens. Among them, 3 groups were used as drug groups, one group as a model group, one group as a diclazuril group, and one group as a blank control group. Each chicken in the drug groups and the diclazuril group aged 12 days was subject to drug administration, with the drug groups being administrated through mixing with feed and the diclazuril group being administrated through drinking water. Each chicken aged 14 days in the drug groups, the diclazuril group and the model group was orally inoculated with $1.0 \times 10^4$ sporulated oocysts of *Eimeria tenella*. Each experimental chicken in all groups was free to feed and drink water until the test was over on the seventh day.

The experimental design is shown in Table 6.

TABLE 6

The experimental design grouping of Example 3

| Group and drug information | Number of chickens | Dosing concentration | Administration route | Time of administration | Dose for *Eimeria* challenge ($\times 10^4$/pcs) |
|---|---|---|---|---|---|
| Drug group 1 | 30 | 5 kg/ton | Mixing with feed | 2 days before *Eimeria* challenge, a total of 9 days | 1.0 |
| Drug group 2 | 30 | 5 kg/ton | Mixing with feed | 2 days before *Eimeria* challenge, a total of 9 days | 1.0 |
| Drug group 3 | 30 | 5 kg/ton | Mixing with feed | 2 days before *Eimeria* challenge, a total of 9 days | 1.0 |
| Model group | 30 | — | — | — | 1.0 |
| Diclazuril | 30 | 0.2 ml/L | Drinking water | 2 days before *Eimeria* challenge, a total of 9 days | 1.0 |
| Blank control | 30 | — | — | — | — |

In this example, the ACI was calculated in the same way as in Example 1.

The test results of this example are shown in Table 7.

TABLE 7

The test results of Example 3

| Group | Relative weight gain rate/% | Survival rate/% | Lesion value | Oocyst value | ACI value | Relative oocyst production (ROP) | Criteria |
|---|---|---|---|---|---|---|---|
| Drug group 1 | 80.3 | 100 | 10.2 | 20 | 150.1 | 59.3 | Low efficacy |
| Drug group 2 | 89.4 | 100 | 7.6 | 20 | 161.8 | 38.4 | Medium efficacy |
| Drug group 3 | 91.6 | 100 | 5.8 | 5 | 180.8 | 14.6 | High efficacy |
| Model group | 76.3 | 96.7 | 17.9 | 40 | 114.8 | 100 | Inefficacy |
| Diclazuril | 98.4 | 100 | 0 | 0 | 198.4 | 0 | High efficacy |
| Blank control | 100 | 100 | 0 | 0 | 200.0 | 0 | |

Clinical Symptoms

Drug group 3, the diclazuril group and the blank control group had no bloody stool, without obvious abnormality in food intake and water drinking; and a small amount of bloody stool appeared in Drug groups 1 and 2.

From the above results, the therapeutic effect of usnic acid sodium against avian coccidiosis is related to the dose administered, however, a small amount of usnic acid sodium can still play a certain role in the treatment, prevention and relief of avian coccidiosis.

Preferred embodiments of the present invention are described in detail above, however, the present invention is not limited to the specific details of the above embodiments, within the scope of the technical conception of the present invention, a variety of simple variants of the technical solution of the present invention may be performed, these simple variants are all within the scope of protection of the present invention.

Further, any combination may be made among the various embodiments of the present invention, as long as it does not contravene the ideas of the present invention, it shall likewise be regarded as the disclosed content of the present invention.

The invention claimed is:

1. A method for preventing or treating coccidiosis in avian animals, comprising administrating a prophylactically or therapeutically effective amount of usnic acid sodium and glucose in a mass ratio of 1:99 or 3:97 to the avian animals.

2. An anti-avian coccidiosis drug, which comprises usnic acid sodium and glucose in a mass ratio of 1:99 or 3:97.

3. An anti-avian coccidiosis feed additive, wherein the feed additive comprises usnic acid sodium and glucose in a mass ratio of 1:99 or 3:97.

4. The anti-avian coccidiosis feed additive according to claim 3, wherein the feed additive is added in feedstuff in an amount that usnic acid sodium is not less than 0.015‰ by mass.

5. The anti-avian coccidiosis feed additive according to claim 4, wherein the feed additive is added in feedstuff in an amount that usnic acid sodium is not less than 0.05‰ by mass.

* * * * *